United States Patent [19]

Nohda

[11] Patent Number: 4,526,451
[45] Date of Patent: Jul. 2, 1985

[54] APPARATUS FOR MEASURING THE REFRACTIVE POWER OF AN OPTICAL SYSTEM

[75] Inventor: Masao Nohda, Yokosuka, Japan

[73] Assignee: Nippon Kogaku K.K., Tokyo, Japan

[21] Appl. No.: 362,598

[22] Filed: Mar. 29, 1982

[30] Foreign Application Priority Data

Apr. 4, 1981 [JP] Japan ................................. 56-50790

[51] Int. Cl.³ ............................................. A61B 3/10
[52] U.S. Cl. ..................................... 351/211; 356/126
[58] Field of Search ....................... 351/205, 211, 221; 356/126

[56] References Cited

U.S. PATENT DOCUMENTS 3,136,839 6/1964 Safir ........................................ 88/56
3,715,166 2/1973 Leighty et al. ..................... 356/125

Primary Examiner—Rodney B. Bovernick
Attorney, Agent, or Firm—Shapiro and Shapiro

[57] ABSTRACT

An apparatus in which an optical system to be examined is periodically scanned by a slit-like illuminating light beam and the light beam from the optical system is received by two pairs of photoelectric converters and the refractive power of the optical system is measured on the basis of the phase difference between the output signals of the photoelectric converters forming each of said pairs includes projection means capable of alternatively scanning the illuminating light beam from two known directions, output means adapted to put out a discrimination signal of the scanning direction of the illuminating light beam, and operational means for receiving the discrimination signal and the phase difference as inputs and obtaining a refractive power.

8 Claims, 15 Drawing Figures

APPARATUS FOR MEASURING THE REFRACTIVE POWER OF AN OPTICAL SYSTEM

BACKGROUND OF THE INVENTION

1. Field of the Invention

This invention relates to an apparatus for measuring the refractive power of an optical system, such apparatus being utilizable as an eye-refractometer device, an automatic lens meter or the like.

2. Description of the Prior Art

An example of the eye-refractometer device will hereinafter be described.

Generally, in the measurement of the refractive power of an eye, it is necessary to measure the astigmatism main diametral line direction and the refractive power in that direction. Apparatus for effecting such measurement on the basis of the principle of the skiascopy are already known. The skiascopy is a method wherein when a slit-like light beam is moved in the pupil of an eye to be examined, the movement of the reflected light from the fundus of the eye is observed and a so-called neutral condition in which light does not move is caused to appear, whereby the refractive power of the eye to be examined is measured. To cause such neutral condition to appear, there is a method wherein lenses having various refractive powers are disposed immediately before the eye to be examined and the eye is observed from a predetermined position, so that the refractive power of the eye is obtained by a lens which brings about the neutral condition, and a method wherein the eye is observed with the observation distance being changed and the refractive power of the eye is obtained from a distance which provides the neutral condition. As an apparatus for photoelectrically measuring the refractive power of an eye by the skiascopy, an apparatus using the former method is disclosed in U.S. Pat. No. 3,136,839 and an apparatus using the latter method is disclosed in U.S. Pat. No. 3,715,166. In these measuring apparatus, the entire apparatus is rotated to detect the astigmatism axis direction of an eye to be examined and an accurate servo mechanism for making the entire apparatus exactly coincident with the main diametral line direction is indispensable. This has led to complexity and bulkiness of the apparatus and has been disadvantageous for quick measurement.

To overcome such disadvantages, a method of knowing the refractive power of an eye from the speed and direction of movement of the reflected light from the fundus of the eye is known, for example, from Japanese Laid-open Patent Application No. 160538/1980 (corresponding U.S. application Ser. No. 152,602 now U.S. Pat. No. 4,353,625). That is, an eye-refractometer using this method has a beam splitter; a projection optical system disposed in one optical path of said beam splitter to project a beam of light into the pupil of an eye to be examined therethrough and to effect scanning linearly thereof; a condensing optical system including a condenser lens fixedly provided in the other optical path of said beam splitter; a diaphragm member fixedly provided behind said condenser lens and a light receiving member fixedly provided further behind said diaphragm member at a conjugate point with the cornea of said eye relative to said condenser lens, said condensing optical system being disposed to condense the reflected light from the fundus of said eye on said light receiving member through said beam splitter; a beam rotating member disposed at the eye side of said beam splitter to rotate the beam about the center of the optical path as its rotational axis; and a signal processing system for processing the signals coming from said light receiving member. However, this device requires an image rotating prism for rotating the light beam to detect the main diametral line direction of astigmatism, but it is considerably difficult in manufacture and adjustment and time-consuming to rotate such image rotating prism about the optical axis without any error.

In view of the fact that an eye can be regarded as an optical system, it is a matter of course that the eye-refractometer as described above can be used as an apparatus for measuring the refractive power of an optical system such as a spectacle lens, without being changed in principle, and in that case, of course, the foregoing discussion likewise holds true.

SUMMARY OF THE INVENTION

It is an object of the present invention to provide an apparatus for measuring the refractive power of an optical system (for example, an eye or spectacle lens) which is easy to manufacture and improved in measurement accuracy.

The invention will become fully apparent from the following detailed description thereof taken in conjunction with the accompanying drawings.

DESCRIPTION OF THE PREFERRED EMBODIMENTS

Figure 1:
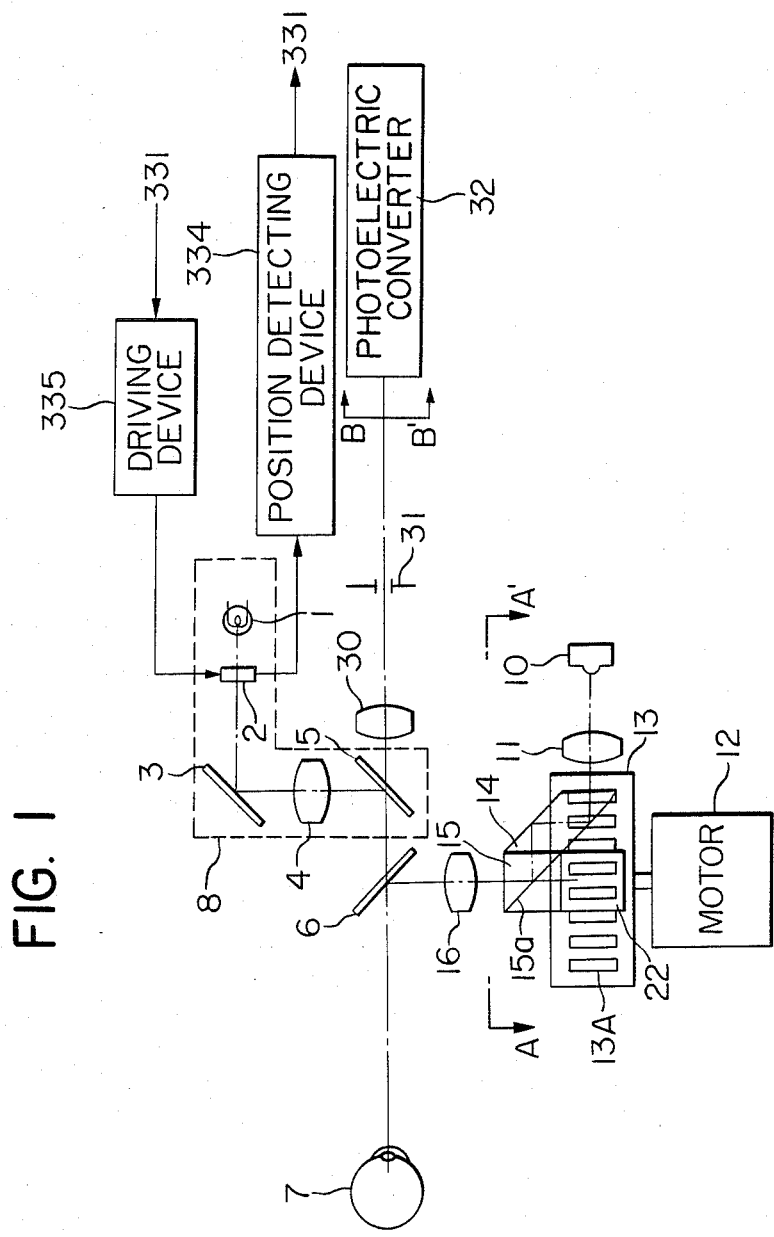
FIG. 1 shows the construction of the optical system according to an embodiment of the present invention.

The invention will hereinafter be described with respect to some embodiments thereof shown in the drawings.

Figure 2:
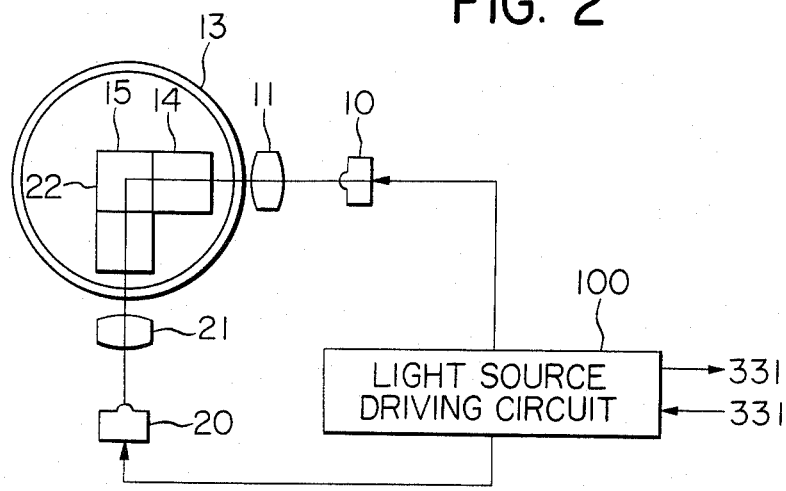
FIG. 2 is a view taken along arrow A—A' in FIG. 1.
Figure 3:
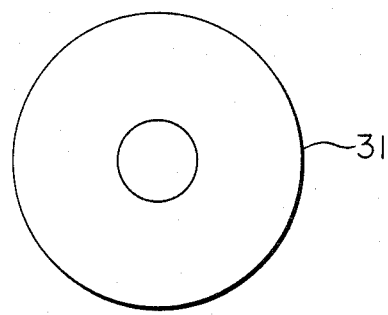
FIG. 3 is a plan view of the diaphragm in FIG. 1.
Figure 4:
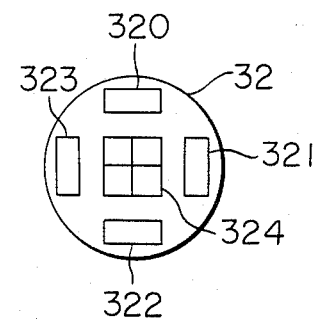
FIG. 4 is a view taken along arrow B—B' in FIG. 1.

FIG. 1 shows the construction of the optical system according to an embodiment of the present invention, FIG. 2 is a view taken along arrow A—A' of FIG. 1, FIG. 3 is a plan view of the diaphragm of FIG. 1, and FIG. 4 is a view taken along arrow B—B' of FIG. 1.

A light source 1 illuminates a fixed view target 2, and the light beam from the fixed view target 2 is reflected by a reflecting mirror 3 and substantially collimated into a parallel light beam by a collimator lens 4. This light beam is reflected by a first optical path splitter 5, whereafter it passes through a second optical path splitter 6 to reach an eye 7 to be examined, which fixedly views the fixed view target 2. The fixed view target 2 is movable in the direction of the optical axis by a driving device 335. As will later be described, the driving device 335 is controlled by the output of an operational circuit 331 so that it can move the fixed view target 2 to a position whereat the eye 7 to be examined can fixedly view in a non-adjusted condition, and constitutes a so-called automatic cloud-mist device. The light source 1, the fixed view target 2, the reflecting mirror 3, the collimator lens 4 and the first optical path splitter 5 together constitute a fixed view target optical system 8.

A projection device has a mechanism for alternatively scanning a slit-like light beam only in orthogonal diametral line directions (the plane of the drawing sheet and a direction perpendicular to the plane of the drawing sheet). That is, as is apparent from FIG. 2, two light sources 10 and 20 disposed with their optical axes being orthogonal to each other are light sources such as infrared ray light-emitting diodes and are alternatively turned on by a driving circuit 100. The light beam from the light source 10 passes through a lens 11, whereafter it passes through slit-like openings 13A formed at predetermined intervals on the side surface of a rotational cylinder 13 rotated by a motor 12 and enters a prism 14 for changing the optical path onto the plane of the drawing sheet of FIG. 1. The lengthwise direction of the slit-like openings 13A is the vertical direction in the plane of the drawing sheet of FIG. 1. The light beam twice reflected in the prism 14 and having left the prism 14 enters a prism 15 and is further reflected by the optical path splitting surface 15a of the prism 15. The light beam having left the prism 15 passes through a lens 16, whereafter it is reflected by the second optical path splitter 6 toward the eye 7 to be examined. By the lenses 11 and 16, the light source 10 is made substantially conjugate with the cornea of the eye 7 to be examined, and if the eye 7 to be examined is an orthoptic eye, the slit-like openings 13A are made substantially conjugate with the fundus of the eye 7 by the lens 16. Accordingly, when the rotational cylinder 13 is rotated, the eye 7 is scanned by a slit-like light beam in a diametral line direction perpendicular to the plane of the drawing sheet of FIG. 1 through the light source 10, lens 11, rotational cylinder 13, prisms 14, 15, lens 16 and second optical path splitter 6.

On the other hand, the light beam from the light source 20 passes through a lens 21, whereafter it enters the rotational cylinder 13 from this side of the plane of the drawing sheet of FIG. 1, and the light beam passed through the slit-like openings 13A enters a prism 22 for changing the optical path to a direction perpendicular to the plane of the drawing sheet, from a direction perpendicular to the plane of the drawing sheet of FIG. 1. The light beam having its optical path changed in the plane of the drawing sheet passes through the optical path splitting surface 15a of the prism 15 and overlaps the optical path of the light source 10 and travels through the lens 16 and the second optical path splitter 6 toward the eye 7 to be examined. By the lenses 21 and 16, the light source 20 is made substantially conjugate with the cornea of the eye 7 and, if the eye 7 is an orthoptic eye, the slit-like openings 13A are made substantially conjugate with the fundus of the eye 7 by the lens 16. Accordingly, when the rotational cylinder 13 is rotated, the eye 7 to be examined is scanned by a slit-like light beam in the diametral line direction in the plane of the drawing sheet of FIG. 1 through the light source 20, lens 21, rotational cylinder 13, prisms 22, 15, lens 16 and second optical path splitter 6.

Of the light beams projected into the pupil of the eye 7, the light beam reflected by the fundus of the eye passes through the second optical path splitter 6 and the first optical path splitter 5, whereafter it is condensed by a condenser lens 30. A diaphragm 31 (the shape of which as viewed from the direction of the optical axis is shown in FIG. 3) having a circular opening centered at the optical axis is fixedly disposed rearwardly of the condenser lens 30, and a photoelectric converter 32 is fixedly disposed further rearwardly of the condenser lens 30. The positions of the diaphragm 31 and the photoelectric converter 32 on the optical axis are determined such that if the eye 7 is an orthoptic eye, the diaphragm 31 is substantially conjugate with the fundus of the eye and the light receiving surface of the photoelectric converter 32 is substantially conjugate with the cornea of the eye 7. On the light receiving surface of the photoelectric converter 32, there are four photoelectric conversion elements 320, 321, 322 and 323 off the optical axis as shown in FIG. 4 and an alignment four-division photoelectric conversion element 324 having the optical axis as the center of division.

A pair of photoelectric conversion elements 320 and 322 are disposed in the direction of a measuring diametral line, namely, on a line orthogonal to the optical axis in the plane of the drawing sheet of FIG. 1 and symmetrically with the optical axis, and another pair of photoelectric conversion elements 321 and 323 are disposed in the direction of a measuring diametral line orthogonal to said measuring diametral line, namely, on a line in a plane orthogonal to the optical axis and orthogonal to the plane of the drawing sheet of FIG. 1 and to the optical axis and symmetrically with the optical axis. The four-division photoelectric conversion element 324 receives the reflected light from the cornea of the eye 7 for the purpose of alignment. When the alignment between the eye 7 and the measuring apparatus of the embodiment is completed, a reflected image uniformly enters the respective elements of the four-division photoelectric conversion element 324 and therefore, the outputs of the respective elements become equal, but when the alignment is insufficient, the outputs of the respective elements do not become equal and it is possible to know the direction of deviation from the magnitudes of the outputs.

Figure 5:
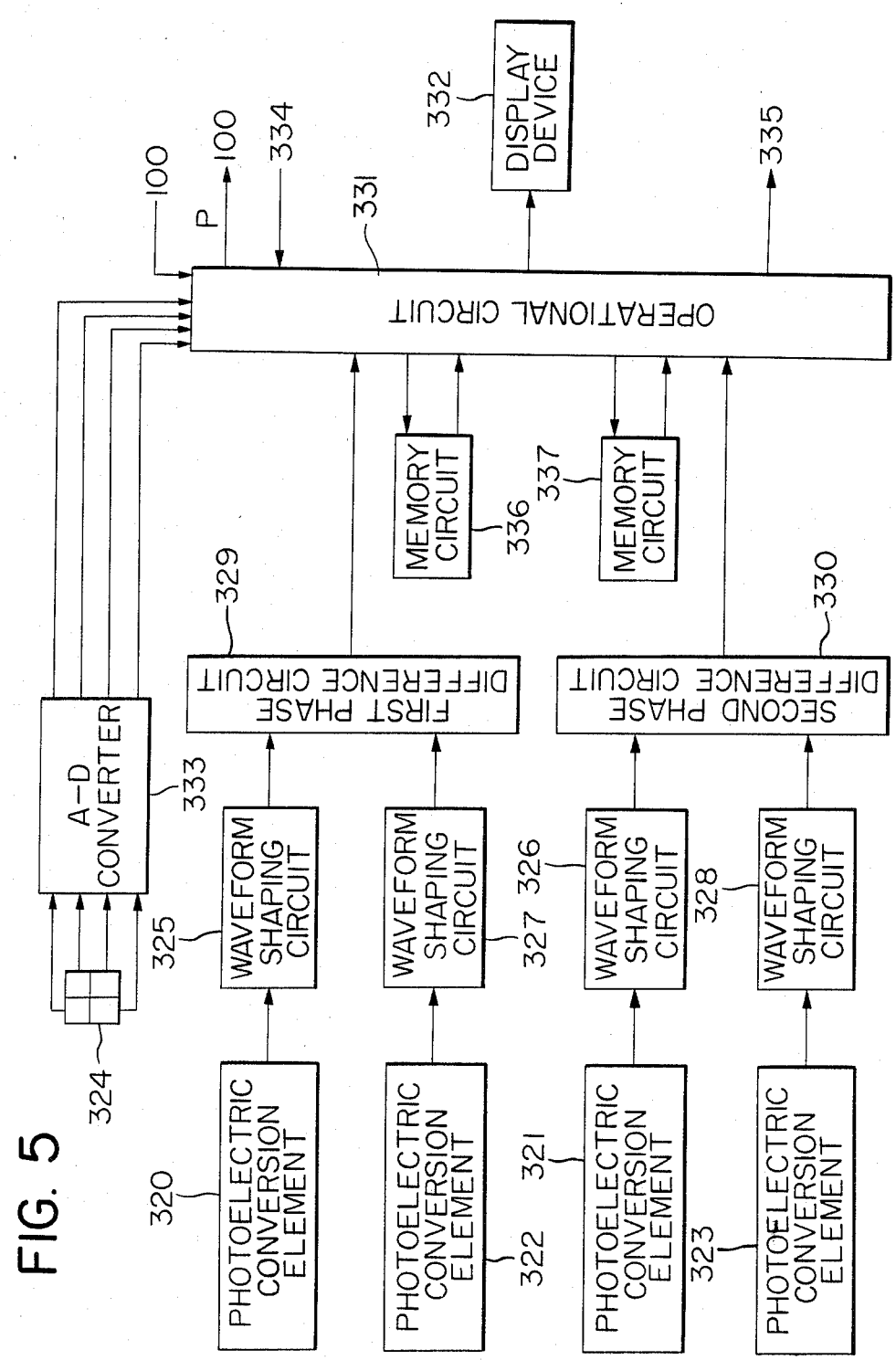
FIG. 5 is a diagram of the circuit in said embodiment.

As shown in FIG. 5, the photoelectric conversion elements 320, 321, 322 and 323 are connected to waveform shaping circuits 325, 326, 327 and 328, respectively. A pair of waveform shaping circuits 325 and 327 for waveform-shaping the output signals of a pair of photoelectric conversion elements 320 and 322 are connected to a first phase difference circuit 329, and a pair of waveform shaping circuits 326 and 328 for waveform-shaping the output signals of a pair of photoelectric conversion elements 321 and 323 are connected to a second phase difference circuit 330. The first phase difference circuit 329 and the second phase difference circuit 330 are connected to an operational circuit 331. A discrimination signal discriminating whether the light source 10 or the light source 20 are being driven is applied as input to the operational circuit 331 from the driving circuit 100 of the light sources 10 and 20. The operational circuit 331 causes the outputs of the first phase difference circuit 329 and the second phase difference circuit 330 when the light source 10 is being driven and the outputs of the first phase difference circuit 329 and the second phase difference circuit 330 when the light source 20 is being driven to be stored in memory circuits 336 and 337, respectively, and thereafter effects an operation between the stored values to determine the direction $\theta$ of astigmatism main diametral line, a spherical surface refractive power s and a cylindrical surface refractive power c, and causes the result thereof to be displayed on a display device 332.

On the other hand, the output of each element of the four-division photoelectric conversion element 324 is converted into a digital signal by an A-D converter 333, whereafter it is applied as input to the operational circuit 331. The operational circuit 331 compares the magnitude and the maximum value of the signal from each element and applies to the display device 332 a signal indicative of the direction for alignment orthogonal to the optical axis and the amount of movement in the direction of the optical axis. The operational circuit 331 further receives as input the output of a position detecting device 334 which detects the position of the fixed view target 2 on the optical axis and sends a signal to the driving device 335 of the fixed view target 2 such that it moves the fixed view target 2 successively in predetermined steps in a direction in which the determined spherical surface refractive power s and cylindrical surface refractive power c decrease. That is, the fixed view target 2, the position detecting device 334, the operational device 331 and the driving device 335 together constitute an automatic cloud-mist device as disclosed in U.S. Pat. No. 4,190,332.

Description will now be made of the operation of the refractometer device whose construction has been described above.

First, assume that the light source 10 is turned on by the light source driving circuit 100. That is, the eye 7 to be examined is scanned by a slit-like light beam along the diametral line in a direction perpendicular to the plane of the drawing sheet. The examiner carries out the alignment between the eye 7 and the refractometer device while seeing the display on the display device 332. When an unshown measuring switch is closed after the alignment has been completed, measurement is started.

The operational circuit 331 detects the turn-on of the light source 10 by the signal from the driving circuit 100 and causes the phase difference obtained from the phase difference measuring circuits 329 and 330 (the phase difference is usually the average value of the measurements effected a number of times) to be stored in the memory circuit 336. When the storage is completed, a light source change-over signal P is applied as input to the driving circuit 100, whereby the light source 10 is turned off and the light source 20 is turned on. The operational circuit 331 detects the turn-on of the light source 20 by the signal from the driving circuit 100 and causes the phase difference obtained from the phase difference measuring circuits 329 and 330 to be stored in the memory circuit 337. When the storage is completed, the operational circuit 331 reads out the stored values in the memory circuits 336 and 337 and determines the refractive power of the eye 7 to be examined.

Figure 10:
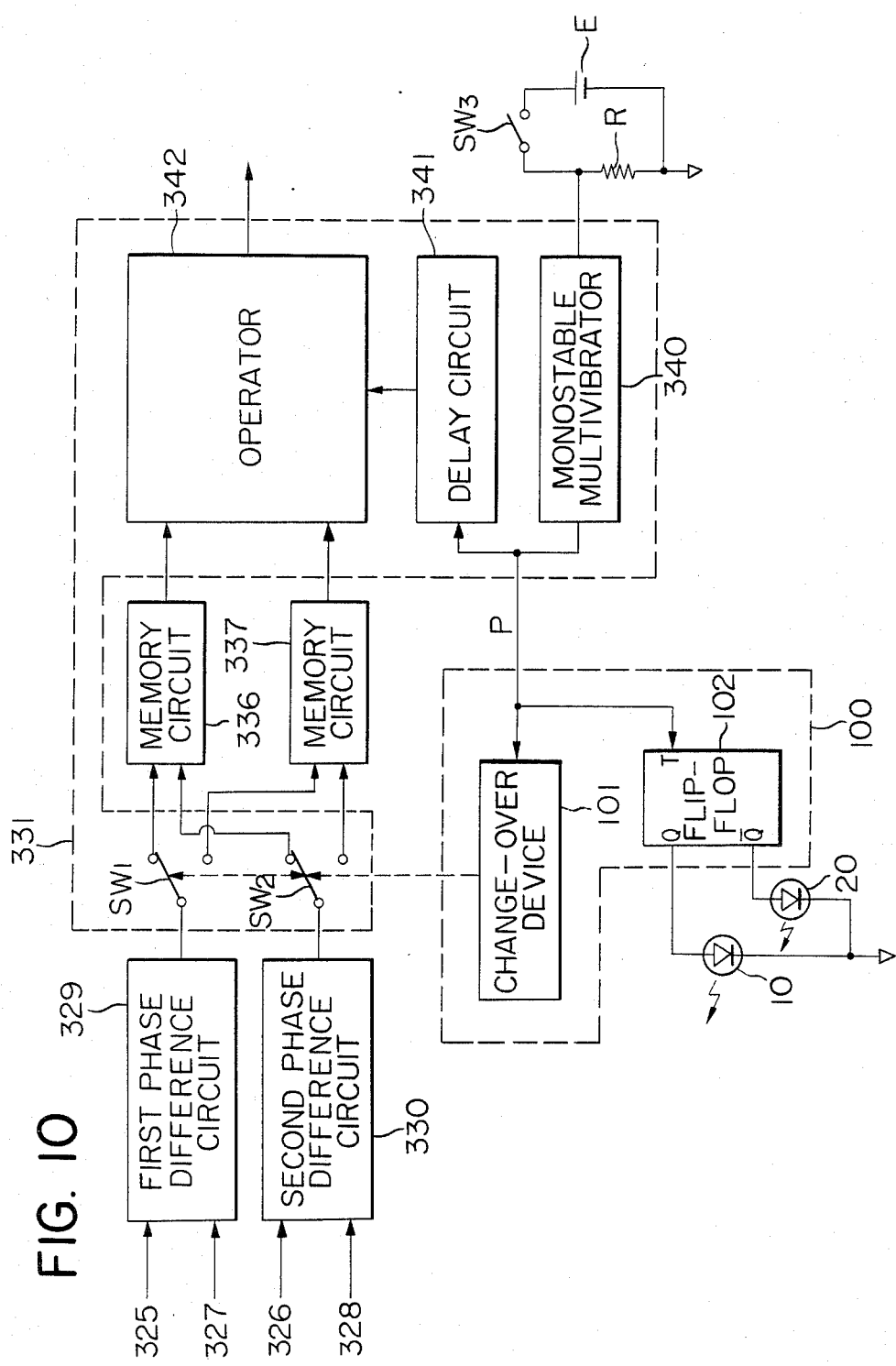
FIG. 10 is an embodiment shown to illustrate the relation between an operational circuit and a driving circuit.

The operational circuit 331 is usually designed in software by the use of a computer, but to describe comprehensibly the relation between the operational circuit 331 and the driving circuit 100, an example designed in hardware is shown in FIG. 10. That is, the operational circuit 331 has a first switch SW1 for changing over the output terminal of the phase difference measuring circuit 329 to the memory circuits 336 and 337, and a second switch SW2 for changing over the output terminal of the phase difference measuring circuit 330 to the memory circuits 336 and 337. The first switch SW1 and the second switch SW2 are interlocking switches and in the figure, the first switch SW1 and the second switch SW2 are connected to the memory circuit 336. The first and second switches SW1 and SW2, with an unshown magnet of the change-over device 101 of the driving circuit 100, constitute a relay device. A measuring switch SW3 has one end thereof connected to the positive pole of a power source E and the other end connected to one end of a resistor R. The other end of the resistor R is connected to the negative pole of the power source E, and the negative pole of the power source E is at a reference potential. The measuring switch SW3, the power source E and the resistor R together constitute a device for generating a measurement starting signal. The other end of the measuring switch SW3 is connected to the monostable multivibrator 340 of the operational circuit 331. The monostable multivibrator 340 produces a pulse of predetermined width at the rising of an input signal produced upon closing of the measuring switch SW3. The output terminal of the monostable multivibrator 340 is connected to a delay circuit 341. The delay circuit 341 delays the pulse of the monostable multivibrator 340 by a sufficient time for the memory circuit 337 to store an input signal after the first and second switches SW1 and SW2 have been changed over, whereafter it causes an operation starting signal to be applied as input to an operator 342. The pulse of the monostable multivibrator 340 is applied as a change-over signal to the T input terminal of a flip-flop (T-flip-flop) 102 and to the change-over device 101 of the driving circuit 100. The flip-flop 102 inverts the output thereof at the falling of the input pulse, and turns off the light source 10 and turns on the light source 20. The changeover device 101 changes over the first switch SW1 and the second switch SW2 at the rising of the input pulse. That is, the first switch SW1 and the second switch SW2 are now connected to the memory circuit 336 and therefore, they are changed over so that they are connected to the memory circuit 337. With such construction, when the measuring switch SW3 is closed, the first switch SW1 and the second switch SW2 are changed over from the memory circuit 336 to the memory circuit 337 and therefore, the phase difference immediately before the measuring switch SW3 is closed is stored in the memory circuit 336. By the falling of the pulse of the monostable multivibrator 340, the light source 20 is turned on and by this time, the first swtich SW1 and the second switch SW2 have already been connected to the memory circuit 337 due to the pulse width of the monostable multivibrator 340 and therefore, the phase difference by the turn-on of the light source 20 is stored in the memory circuit 337. The pulse of the monostable multivibrator 340 is delayed by a sufficient time for the memory circuit 337 to store by the delay circuit 341, whereafter it is applied as the storage completion signal to the operator 342 and therefore, the operator 342 effects a predetermined operation necessary to obtain a refractive power or the like and produces the result thereof. The automatic cloud-mist device is operated on the basis of this refractive power, and the above-described operation is repeated at each step and when the refractive power has become invariable, the then refractive power (s, c, $\theta$) is displayed by the display device 332. Until the automatic cloud-mist is completed, the measurement only of the light source 10 may suffice. This will more specifically be described.

Figure 6A:
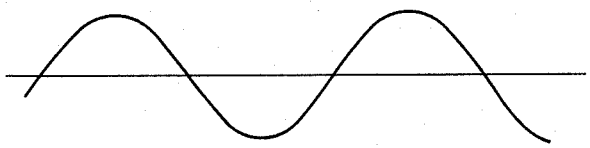
FIGS. 6A–6D are a graph showing the signals obtained from photoelectric conversion elements.
Figure 6B:
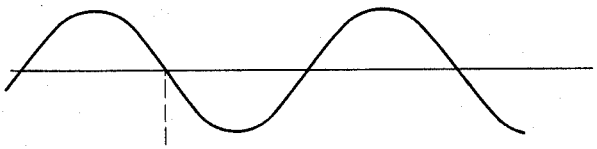
Figure 6C:
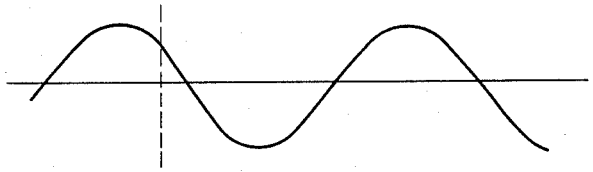
Figure 6D:
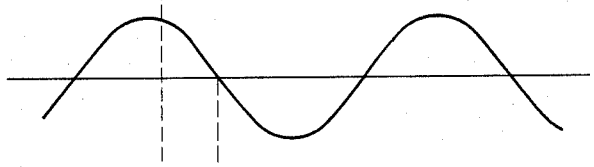

If there is no astigmatism in the eye 7 to be examined, the slit-like light beam is not rotated by the eye 7. The slit-like light beam reflected by the fundus of the eye runs on the photoelectric converter 32 at a speed corresponding to the refractive power of the eye 7. When the light source 10 is on, the scanning direction of the slit-like light beam does not vary and therefore, as shown in FIGS. 6A and 6C, entirely identical signals are obtained from the photoelectric conversion elements 320 and 322, and as shown in FIGS. 6B and 6D, out-of-phase signals corresponding to the speed of the slit-like light beam on the photoelectric converter 32 are obtained from the photoelectric conversion elements 321 and 323. Accordingly, if the phase difference between the signals obtained from the photoelectric conversion elements 321 and 323 is $\phi_1$, the output of the first phase difference circuit 329 exhibits $\phi_{329}=0$ and the output of the second phase difference circuit 330 exhibits $\phi_{330}=\phi_1$. The operational circuit 331 causes the memory circuit 336 to store $\phi_{329}=0$ and $\phi_{330}=\phi_1$.

When the measurement in the first diametral line direction is completed, the driving circuit 100 turns off the light source 10 and turns on the light source 20 by the change-over signal P from the operational circuit 331. Thereupon, the eye 7 to be examined is scanned by the slit-like light beam in the diametral line direction on the plane of the drawing sheet. If there is no astigmatism in the eye 7 as has been assumed above, the eye 7 has a spherical surface refractive power s equal on all diametral lines and therefore, as a matter of course, the output of the first phase difference circuit 329 exhibits $\phi_{329}=\phi_1$ and the output of the second phase different circuit 330 exhibits $\phi_{330}=0$ and accordingly, the operational circuit 331 causes the memory circuit 337 to store $\phi_{329}=\phi_1$ and $\phi_{330}=0$. The operational circuit 331 reads out the measurement values in the first and second diametral line directions stored in the memory circuit 336 and 337, and determines the refractive power (spherical surface refractive power s, cylindrical surface refractive power 0, astigmatism axis o). In this case, the outputs $\phi_1$ of the first phase difference circuit 329 and the second phase difference circuit 330 correspond to the spherical surface refractive power s of the eye 7 to be examined. The operational circuit 331 detects, by the positive or the negative of the spherical surface refractive power, whether the eye 7 is short-sighted or long-sighted, and applies a signal to a moving circuit 335 for the fixed view target 2 so as to move the fixed view target 2 in a direction in which the eye 7 is loosened. In this manner, the operational circuit 331 causes the display device 332 to display the refractive power when the refractive power (in this case, the spherical surface refractive power s) has become invariable, even if the fixed view target 2 is varied further.

Figures 7A, 7B, 7C:
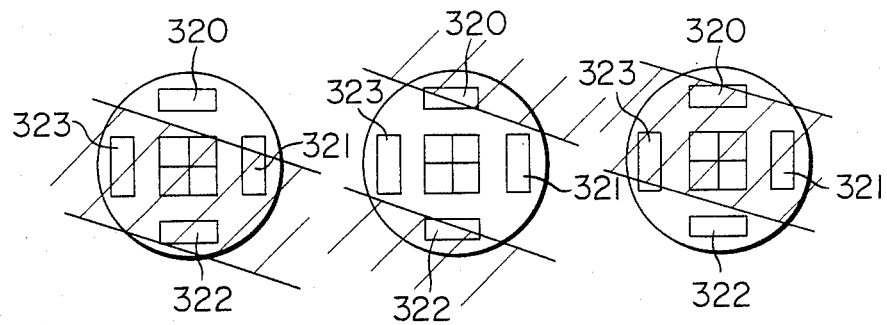
FIGS. 7A, 7B and 7C illustrate the scanning of a slit-like light beam.

If there is astigmatism in the eye 7 to be examined, the slit-like light beam is twisted by an angle $\theta$ corresponding to the scanning direction and the astigmatism main diametral line direction by the eye 7, as is well known. As a result, the slit-like light beam obliquely inclined in the order as shown in FIG. 7A, 7B and 7C runs on the light receiving surface of the photoelectric converter 32. Of couse, this is a general case and, in a special case, that is, when the astigmatism main diametral line direction is $\theta=0, 90$ (that is, the direction perpendicular to the plane of the drawing sheet), the twist of the slit-like light beam by the eye 7 does not occur. In this special case, when the light source 10 is turned on, the first phase difference circuit 329 produces a phase difference $\phi_{329}=0$ and the second phase difference circuit 330 generates a phase difference $\phi_{330}=\phi_2$. When the light source 20 is turned on, the first phase difference circuit 329 produces a phase difference $\phi_{329}=\phi_3$ and the second phase difference circuit 330 generates a phase difference $\phi_{330}=0$. Here, $\phi_2\neq\phi_3$.

Figure 8:
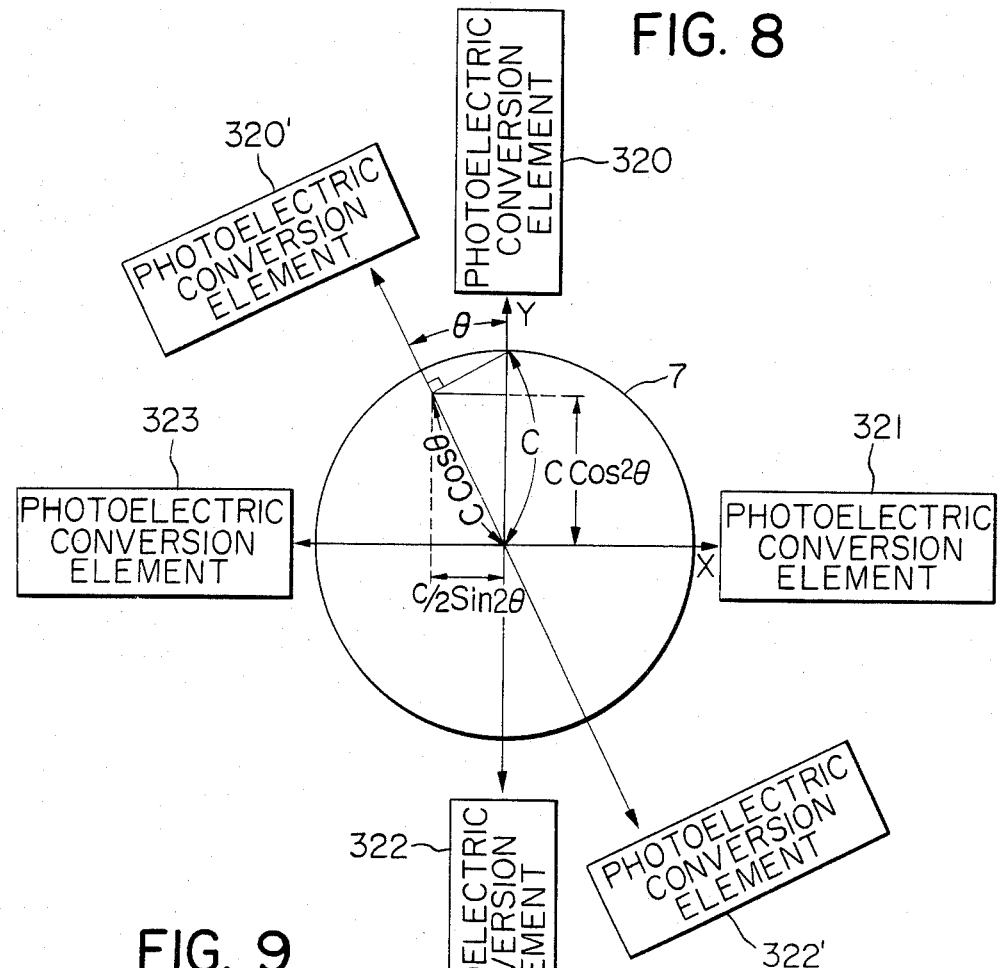
FIG. 8 illustrates the connection between an eye to be examined and photoelectric conversion elements.

In such a case, the twist angle $\theta$ may be regarded as $\theta=0$ in the generalized example as described above. When the light receiving surface is scanned as shown in FIGS. 7A, 7B and 7C, a phase difference is produced between the outputs of the pair of photoelectric conversion elements 320 and 322 and between the outputs of the other pair of photoelectric conversion elements 321 and 323. Reference is now had to FIG. 8 to describe what information the then phase differences $\phi_4$ and $\phi_5$ have. In FIG. 8, X and Y are measuring diametral line directions and in other words, X is the direction of movement of the slit-like light beam on the eye 7 when the light source 10 has been turned on and Y is the direction of movement of the slit-like light beam on the eye 7 when the light source 20 has been turned on. Now, assuming that the main diametral line direction of the eye 7 is inclined by $\theta$ with the scanning direction Y of the slit-like light beam when the light source 20 has been turned on as the reference, the scanning direction of the slit-like light beam on the light-receiving surface of the photoelectric converter 32 is inclined by $\theta$ with respect to Y direction if the light source 20 is turned on. Accordingly, if, as shown in FIG. 8, photoelectric conversion elements 320' and 322' are disposed in this direction inclined by $\theta$, a value comprising an elliptical refractive power $C \cos \theta$ in Y direction plus the spherical surface refractive power s will be obtained as the phase difference between the photoelectric conversion elements 320' and 322', but since, in the refractive power measuring apparatus of FIG. 1, the photoelectric conversion elements 320 and 322 are disposed in Y direction, the value obtained as the phase difference between the photoelectric conversion elements 320 and 322 is the projected value of the elliptical refractive power $C \cos \theta$ in Y direction, namely, $C \cos \theta \cdot \cos \theta$ plus the spherical surface refractive power s. Accordingly, the value $D_1$ obtained from the phase difference $\phi_4$ between the output signals of the photoelectric conversion elements 320 and 322 is $$d_1 = S + C \cos^2 \theta \tag{1}$$

On the other hand, the scanning direction of the slit-like light beam is twisted by $\theta$ from Y direction, whereby X direction component is also produced. However, the component of the twist depends only on the cylindrical surface and the spherical surface refractive power does not have a component which contributes to the component of the twist and therefore, the phase difference $\phi_5$ between the photoelectric conversion elements 321 and 323 corresponds only to the X direction component of the previously described $C \cos \theta$, namely, $C \cos \theta \cdot \sin \theta$. Accordingly, the value $D_2$ obtained from the phase difference between the output signals of the photoelectric conversion elements 321 and 323 is $$D_2 = C\cos\theta \cdot \sin\theta = \frac{C}{2} \sin 2\theta \tag{2}$$

Next, if the light source 10 is turned on and the slit-like light beam is scanned in X direction, the value $D_3$ obtained from the phase difference between the photoelectric conversion elements 321 and 323 is $$D_3 S + C \cos^2(\theta + 90) = S + C \sin^2 \theta \quad (3)$$

Likewise, the value $D_4$ obtained from the phase difference between the photoelectric conversion elements 320 and 322 is $$D_4 = \frac{C}{2} \sin 2(\theta + 90) = -\frac{C}{2} \sin 2\theta \quad (4)$$

In the above-described embodiment, the unknown quantities are C, S and $\theta$ and there are three measurement data, $D_1 (=-D_4)$, $D_2$ and $D_3$ and accordingly, by processing equations (1), (2) and (3) (or (4)) in the operational circuit 331, the spherical surface refractive power S, the cylindrical surface refractive power C and the astigmatism main diametral line direction $\theta$ can be obtained. When $\theta=0$, the astigmatism main diametral line direction is coincident with X direction and Y direction and as a matter of course, $D_1 = S + C$ and $D_2 = S$.

However, if design is made such that the operation as described above is effected by the operational circuit 331, much time will be required for the operation or the constants between the outputs of the first and second phase difference circuits 329, 330 and the values $D_1$, $D_2$, $D_3$, $D_4$ will be varied by the arrangement of the optical system. Therefore, in the actual apparatus, after the apparatus has been made, measurement may be effected by the use of a sham eye whose refractive power is pre-known and the then outputs of the phase difference circuits 329 and 330 (two outputs for each scanning direction, totalling four outputs) may be stored in the operational circuit 331 correspondingly to the above-mentioned known refractive power, thereby eliminating the above-noted inconvenience. Since the unknown quantities are three, namely, C, S and $\theta$ and the measurement data are three (actually there are four measurement data, but two of them only differ in sign due to the condition that the astigmatism axes are orthogonal to each other and thus, there are substantially three measurement data), the refractive power (determined by C, S and $\theta$) is primarily determined.

If design is thus made such that the outputs of the first and second phase difference circuits 329 and 330 correspond to the refractive power, the arrangement of the optical system can be made relatively freely without adding any complicated procedure. For example, in FIG. 1, the slit-like openings 13A need not be conjugate with the fundus of the eye 7 to be examined, but it will suffice as a projection device if the eye to be examined can be simply scanned periodically by a slit-like light beam. Further, the diaphragm 31 is movable to any position on the measuring optical axis.

Further, the scanning directions by the projection apparatus need not be coincident with the direction of the pair of photoelectric conversion elements, but if they are only known, they can be determined to free directions. Furthermore, the scanning directions by the projection device need not be made orthogonal to each other if they are only known and the directions of each of the two pairs of photoelectric conversion elements need neither be made orthogonal to each other if they are only known. It is because the unknown quantities are four in total, namely, two astigmatism main diametral line directions and the refractive powers in these directions (from which the spherical surface refractive power S, the cylindrical surface refractive power C and the astigmatism main diametral line direction $\theta$ may be obtained) and the measurement values are also four and therefore certain measurement values (four kinds of phase difference) are in one to one correspondence relationship with the refractive power, and thus a correspondence table may be obtained by the use of the above-described sham eye and this may be placed into the operational circuit 331, whereby a very simple operation may be effected without a complicated calculation being carried out.

While the foregoing description has been made with respect to an eye-refractometer device, the above-described device can also be used as a lens meter without any change being added thereto. In the case of the measurement of an eye refractive power, constructional features lie in that the illuminating light beam passes twice through the examined optical system (the crystalline lens of the eye 7 to be examined) to measure the reflected light beam on the fundus of the eye and that the projection optical path and the measuring optical path are partly common to each other, but usually in the case of a lens meter, measurement can be accomplished by the illuminating light beam passing once through the examined lens, and the projection optical path and the measuring optical path are formed on the opposite sides of the examined lens. Of course, if design is made such that the light beam passed through the examined lens is caused to again enter the examined lens by a reflecting mirror, there can be achieved a construction similar to the above-described eye-refractometer device.

Figure 9:
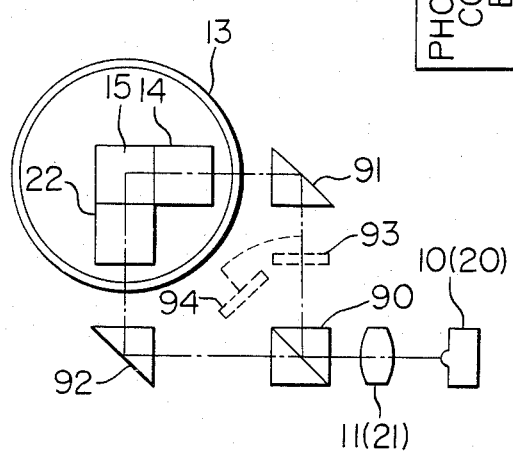
FIG. 9 is a view corresponding to FIG. 2 but showing another embodiment.

In the above-described embodiment shown in FIGS. 1 to 6A–6D the rotational cylinder 13 is the only movable member and therefore, optically delicate adjustment is not required. This embodiment is excellent in that the change-over operation of the optical path by the examiner is unnecessary and to achieve the object of the present invention, design may also be made such that the light sources 10 and 20 are normally turned on and a light-intercepting plate is alternatively inserted in front of the light sources 10 and 20. In this case, a discrimination signal as to which of the optical paths has been selected may be obtained in association with the light-intercepting plate. Also, if the light-intercepting plate is used, one of light sources 10 and 20 and one of lenses 11 and 21 may be provided as shown in FIG. 9 (which corresponds to FIG. 2). In FIG. 9, reference numeral 90 designates a beam splitter and prisms 91 and 92 are for changing the optical path by 90°. Light-intercepting plates 93 and 94 are formed integrally with each other and are rotatively movable on a circle substantially centered at the point of intersection between the three optical axes of the beam splitter 90 by an unshown mechanism so as to alternatively select a desired optical path, and a discrimination signal as to which of the optical paths has been selected may be obtained by an unshown detecting switch (a mechanical switch, a photoelectric switch or the like). Of course, design may also be made such that the examiner does not manually effect the optical path change-over but an optical path can be automatically selected by a motor or the like. This is not a construction in which an optical member is moved and therefore, a rough construction will suffice.

Also, instead of using the light-intercepting plates 93 and 94, a chopper 13 may be made to serve also as the light-intercepting plates 93 and 94 by suitably determining the pitch of the openings in the chopper 13. That is, the pitch of the openings in the chopper 13 may be determined such that the optical path from the prism 91 is intercepted when the optical path from the prism 92 has been formed. In an extreme case, two openings may be provided at mutually opposed positions.

According to the present invention, as has been described above, there can be obtained a measuring apparatus which is easy to manufacture and yet capable of well measuring the refractive power of an optical system which has been improved in measurement accuracy.

I claim:

1. An apparatus in which an optical system to be examined is periodically scanned by a slit-like illuminating light beam and light emanating from the optical system in response to the scanning is received by two pairs of photoelectric converters and the refractive power of said optical system is measured on the basis of the phase difference between the output signals of the photoelectric converters forming each of said pairs, said apparatus including:

projection means capable of alternatively scanning said optical system with said illuminating light beam from two known directions, output means adapted to produce a discrimination signal of the scanning direction of said illuminating light beam, and operational means for receiving said discrimination signal and said phase difference as inputs and determining the refractive power of the optical system.

2. An apparatus according to claim 1, wherein said projection means includes a pair of light sources disposed with their optical axes orthogonal to each other, a driving circuit for alternatively turning on said light sources, a pair of lenses disposed on the optical axes of said light sources, a rotatable cylinder provided with a number of slits and disposed to intercept light from said sources transmitted by said lenses, and a pair of prisms for reflecting the intercepted light from each of said light sources toward a further prism.

3. An apparatus for measuring the refractive power of an optical system comprising:

(a) scan means which selectively scans the optical system by means of a slit-like illuminating light beam from two known directions and which generates a discrimination signal of the scanning direction of said illuminating light beam;

(b) two pairs of photoelectric converting means for receiving said illuminating light beam through said optical system;

(c) phase difference measuring means which produces a phase difference signal corresponding to the phase difference between the output signals of the photoelectric converting means forming each of said pairs; and (d) operational means for receiving said discrimination signal and said phase difference as inputs and obtaining a refractive power of said optical system.

4. An apparatus according to claim 3, wherein said scan means includes a cylinder provided with a number of slits arranged substantially equidistant along its periphery, rotating means for rotating the cylinder at a constant frequency, light source means capable of illuminating said cylinder from two predetermined directions and disposed orthogonal to the outer surface of said cylinder, selection means for selectively selecting the illumination directions of the cylinder by the light source means, and prism means for receiving as inputs a light beam from one of said two predetermined directions which passes through the slits of said cylinder and a light beam from the other direction, and for converting the orientations of the light beams and making the two light beams coincident with each other in such a manner that slit-like illumination light beams scan said optical system from two directions.

5. An apparatus according to claim 4, wherein said two predetermined directions in which said light source means is capable of illuminating said cylinder are orthogonal to each other, and wherein said two directions of said slit-like illumination light beams whose orientations are converted by said prism means are orthogonal to each other.

6. An apparatus according to claim 5, wherein said light source means includes two light sources which are arranged in said predetermined directions orthogonal to each other and wherein said selection means is light source driving means which drives selectively said two light sources.

7. An apparatus according to claim 4, wherein said selection means is interception means which selectively intercepts light beams from said predetermined directions.

8. An apparatus according to claim 6, wherein said prism means includes the following surfaces:

a first reflection surface for turning by 90° the optical axis of the light beam from said one direction, an optical path splitting surface for transmitting the light beam reflected at the first reflection surface, a second reflection surface for turning by 90° the optical axis of the light beam from said other direction in such a manner that the optical axis of the light beam from the other direction is made parallel to the optical axis of the light beam reflected at the first reflection surface, and a third reflection surface for turning by 90° the optical axis of the light beam reflected at said second reflection surface in such a manner that the light beam reflected at the second reflection surface is directed toward said optical path splitting surface and is reflected therefrom and the optical axis of the light beam reflected at the optical path splitting surface is coincident with the optical axis of the light beam which is transmitted by the optical path splitting surface.

* * * * *